United States Patent [19]

Micetich et al.

[11] 4,187,221
[45] Feb. 5, 1980

[54] PROCESS FOR PREPARING AZETIDINONES

[75] Inventors: Ronald G. Micetich; Robert A. Fortier, both of Sherwood Park; Chia C. Shaw, Edmonton; Werner O. Merlo, Devon, all of Canada

[73] Assignee: Connlab Holdings Limited, Quebec, Canada

[21] Appl. No.: 864,705

[22] Filed: Dec. 27, 1977

[51] Int. Cl.² .................. C07D 205/08; C07D 403/04
[52] U.S. Cl. ........................... 260/239 A; 260/245.4; 260/326 S; 260/326 N; 260/326.37; 260/330.3; 542/420
[58] Field of Search ... 260/239 AL, 332.2 H, 308 D, 260/307 FA, 326 S, 326.37

[56] References Cited

U.S. PATENT DOCUMENTS

| | | | |
|---|---|---|---|
| 3,840,556 | 10/1974 | Kukolja | 260/326 S |
| 3,962,276 | 6/1976 | Kukolja et al. | 260/376 S |
| 3,989,685 | 11/1976 | Tanida | 260/239.1 |
| 4,009,159 | 2/1977 | Kamiya et al. | 260/239.1 |
| 4,057,540 | 11/1977 | Micetich | 260/239 AL |

FOREIGN PATENT DOCUMENTS

| | | | |
|---|---|---|---|
| 1346744 | 2/1974 | United Kingdom . | |
| 1523885 | 6/1978 | United Kingdom | 260/239 A |

OTHER PUBLICATIONS

Jen et al., J. Organic Chem. 38, 2857 (1973).
Kamiya et al., Tetrahedron Letters 1973, 3001.
Christiansen et al., Chem. Abs. 76, 99685f (1972).
Christiansen et al., Chem. Abs. 77, 126661z (1972).
Kukolja et al., J. Amer. Chem. Soc. 93, 6267 (1971).
Koppel et al., J. Amer. Chem. Soc. 95, 2403 (1973).
Wolfe et al., Can. J. Chem. 50, 2898-2901; 2902-2905 (1972).
Baldwin et al., J. Chem. Soc., Chem. Comm. 1976, 667-668.
Micetich et al., in Beta-Lactam Antibiotics, J. Ellis, Ed. (Chemical Society of London, 1977) Chapter 23.
Flynn, Ed. Cephalosporins and Penicillins, (Academic Press. 1972).

*Primary Examiner*—Mark L. Berch
*Attorney, Agent, or Firm*—Cushman, Darby & Cushman

[57] ABSTRACT

A process for preparing azetidinones of the formulae 1 and 2A and the stereoisomers of the latter of formula 2B

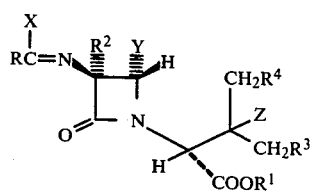

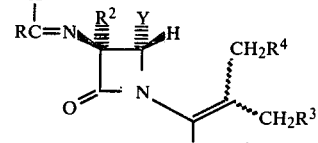

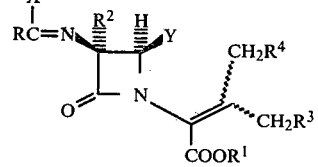

wherein R is an amino-protecting group commonly used in penicillin chemistry and is selected from the group consisting of H, $C_1$-$C_6$ alkyl, phenyl, (optionally substituted in the o-, m-, or p- positions by $CH_3$, F, Cl, $OCH_3$, or a nitro group), benzyl, 2-thienylmethyl, tetrazol (1-, 2-, or 5-)-ylmethyl, 2-phenyl-5-methylisoxazol-4-yl, phenoxymethyl, and $R^5O$— and $R^5S$, wherein $R^5$ stands for $C_1$-$C_6$ alkyl, phenyl, benzyl or trichloroethyl; it should be noted that the value of R is immaterial to the process described;

X is selected from the group consisting of H, SCl, SBr, Cl, Br, and OH. In the case where X is OH the group $RCX=N$— is better represented as the amide, $RCONH$—, group;

$RCX=N$ may also represent the phthalimido, succinimido-, or tritylamino- group;

$R^1$ is a carboxy-protecting group commonly used in penicillin chemistry and is selected from the group consisting of hydrogen, a cleavable acid protecting group selected from $C_1$-$C_6$ alkyl, methoxymethyl, phenoxymethyl, benzyloxymethyl trichloroethyl, benzyl, p-halobenzl, p-nitrobenzl, p-methoxybenzyl, benzhydryl and trimethylsilyl;

$R^2$ is selected from hydrogen and methoxy;

Y and Z are the same or different and each selected from the group consisting of Cl and Br; in addition Z may be I, $OCH_3$, $OCOCH_3$, OCOH, $NO_3$, $N_3$, NH-phenyl, SCl, and SBr;

$R^3$ and $R^4$ are the same or diffferent and each selected from the group consisting of H, Cl, Br, I, SCl, SBr, $OCH_3$, $OC_2H_5$, $OCOCH_3$, OCOH, OH, $SCH_3$, S-phenyl, S-tetrazolyl, S-triazolyl, $N_3$, $NO_3$, CN, $N(CH_3)_2$ and NH-phenyl, with the proviso that one of $R^3$ or $R^4$ must be H and that $R^3$ and $R^4$ may only both be H when X is H or in the compounds of formula 2B, by treating a 2-(substituted methyl)penicillin or a 3,3-disubstituted cepham derivative with a halogenating agent followed by treatment with a base, or by treating an unsym - azetidinone disulfide with a halogenating agent.

These compounds are useful intermediates for the syntheses of modified cephalosporins and of analogues of these compounds in which the sulfur is replaced by oxygen or nitrogen, examples being the so-called 1-oxacephalosporins and 1-azacephalosporins.

11 Claims, No Drawings

PROCESS FOR PREPARING AZETIDINONES

The present invention relates to a convenient, economical, and high-yield process for the preparation of azetidinone derivatives of the general formulae 1, 2A, and 2B, and to the compounds of formula 1 used in said process.

The compounds of formulae 1 and 2A, and the stereoisomers of the latter of formula 2B which are prepared by the process of the present invention correspond to the general formulae

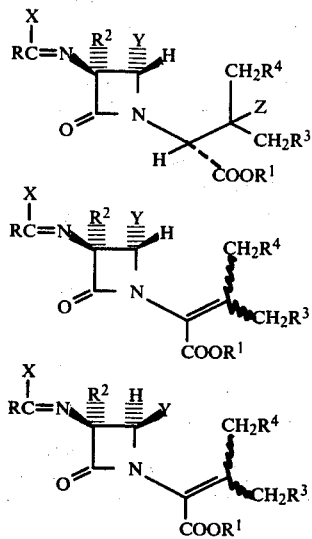

wherein R is an amino-protecting group commonly used in penicillin chemistry and is selected from the group consisting of H, $C_1$–$C_6$ alkyl, phenyl, (optionally substituted in the o-, m-, or p- positions by $CH_3$, F, Cl, $OCH_3$, or a nitro group), benzyl, 2-thienylmethyl, tetrazol (1-, 2-, or 5-)-ylmethyl, 2-phenyl-5-methylisoxazol-4-yl, phenoxymethyl, and $R^5O$— and $R^5S$, wherein $R^5$ stands for $C_1$–$C_6$ alkyl, phenyl, benzyl or trichloroethyl; it should be noted that the value of R is immaterial to the process described;

X is selected from the group consisting of H, SCl, SBr, Cl, Br, and OH. In the case where X is OH the group RCX=N— is better represented as the amide, RCONH—, group;

RCX=N may also represent the phthalimido, succinimido-, or tritylamino-group;

$R^1$ is a carboxy-protecting group commonly used in penicillin chemistry and is selected from the group consisting of hydrogen, a cleavable acid protecting group selected from $C_1$–$C_6$ alkyl, methoxymethyl, phenoxymethyl, benzyloxymethyl trichloroethyl, benzyl, p-halobenzyl, p-nitrobenzyl, p-methoxybenzyl, benzhydryl and trimethylsilyl;

$R^2$ is selected from hydrogen and methoxy;

Y and Z are the same or different and each selected from the group consisting of Cl and Br; in addition Z may be I, $OCH_3$, $OCOCH_3$, OCOH, $NO_3$, $N_3$, NH-phenyl, SCl, and SBr;

$R^3$ and $R^4$ are the same or different and each selected from the group consisting of H, Cl, Br, I, SCl, SBr, $OCH_3$, $OC_2H_5$, $OCOCH_3$, OCOH, OH, $SCH_3$, S-phenyl, S-tetrazolyl, S-triazolyl, $N_3$, $NO_3$, CN, $N(CH_3)_2$ and NH-phenyl, with the proviso that one of $R^3$ or $R^4$ must be H and that $R^3$ and $R^4$ may only both be H when X is H or in the compounds of formula 2B.

In a preferred class of compounds each of $R^3$ and $R^4$ is as defined above except that one of either $R^3$ or $R^4$ must be hydrogen and that both can only be hydrogen when X represents H.

It should be noted that for the purpose of the process of the present invention the values of R and $R^1$ are not critical.

BACKGROUND OF THE INVENTION

The selective opening of the thiazolidine ring of penicillins between the sulphur and carbon atom 5 without affecting the B-lactam ring may be effected by the use of electrophilic agents, preferably agents capable of functioning as a source of positive halogen, as described in Eli Lilly British Pat. No. 1,346,744, published Feb. 13, 1974. Similar ring openings have also been carried out with penicillin sulfoxides, and a comprehensive review of those reactions is found in "Cephalosporins and Penicillins", E. H. Flynn, Ed., Academic Press, New York and London, 1972, chapter 5. The opening of the thiazolidine ring of anhydropenicillin by means of chlorine has been described by Wolfe et al. in Can. J. Chem. 50, 2902 (1972). Depending upon the reaction conditions selected there were obtained either compounds analogous to the compounds of formula 1 of this Application and their respective stereoisomers at C-4, or compounds analogous to the compounds of formulae 2A or 2B of this Application having $R^3$ and $R^4$ in both cases as hydrogen only. Baldwin et al., J.C.S. Chem. Comm. 1976,667, have prepared a compound of formula 1 which differs significantly from the compounds of formula 1 of this invention in having a free hydroxy group as the substituent Z. The transformation of the compounds of the type represented by formula 1 in which $R^3$ and $R^4$ are both hydrogen to the corresponding compounds of the type represented by formulae 2A and 2B by means of triethylamine has been described e.g. by Kukolja et al., J. Am. Chem. Soc. 93,6267(1971), in U.S. Pat. No. 3,840,556 issued Oct. 8, 1974, and in British Patent No. 1,346,744 cited above. Compounds of the formula 1 in which $R^3$ and $R^4$ are both hydrogen have also been described in British patent No. 1,523,885 issued from British patent application 16582/75 which also discloses an alternate method for their preparation. However, all the procedures disclosed in the above references have the disadvantage that the compounds of the type represented by formula 1 in which $R^3$ and $R^4$ are both hydrogen are obtained as mixtures of stereoisomers at C-4, and that such mixtures have to be separated by laborious and expensive chromatographic methods before the individual stereoisomers may be used as starting materials for further syntheses.

SUMMARY DESCRIPTION OF THE INVENTION

The present invention relates to a convenient, economical and high-yield process for preparing compounds of the formulae 1, 2A and 2B, in which R, $R^1$, $R^2$, $R^3$, $R^4$, X, Y, and Z are as defined above. It is a further particular advantage of the process of this invention that the compounds of formula 1 are substantially obtained only in the form of the particular stereoisomer at C-4 represented by formula 1, so that it is not necessary to separate stereoisomers by time-consuming and expensive chromatographic procedures before using them in further synthetic steps. The invention also relates to the compounds 1. The process of this invention is carried out as follows.

A 2-(substituted methyl)penicillin of the formula 3a in which R, $R^1$, and $R^2$ are as defined above, X is OH, $R^3$ is hydrogen, and $R^4$ is a halogen selected from chlorine, bromine or iodine, or an acyloxy group selected from formyloxy and acetoxy, is treated with a halogenating agent selected from the group consisting of chlorine, bromine, sulfuryl chloride, and sulfuryl bromide, preferably sulfuryl chloride. Kukolja et al. cited above had obtained compounds of the type of formula 1 in which $R^3$ and $R^4$ are both hydrogen when treating the corresponding penicillins of formula 3a in which $R^3$ and $R^4$ are hydrogen with one equivalent of sulfuryl chloride, and had obtained the corresponding compounds of the type of formulae 2A and 2B in which $R^3$ and $R^4$ are both hydrogen when treating the corresponding penicillins of formula 3a in which $R^3$ and $R^4$ are hydrogen with two or more equivalents of sulfuryl chloride. We have how found, suprisingly, that the reaction of a substituted penicillin of formula 3a, in which R, $R^1$, $R^2$, $R^3$, $R^4$, are as defined immediately above and X is OH, with one equivalent of sulfuryl chloride is incomplete. However, when using two equivalents or more of sulfuryl chloride, or when using a very large molar excess of sulfuryl chloride both as reactant and as solvent, it was indeed unexpected to find that only the single stereoisomer of the corresponding compound of formula 1 is obtained in which R, $R^1$, $R^2$, $R^3$ and $R^4$ are as defined above, X is OH, Z is SCl, and Y is a chlorine atom trans to the group RC(X)=N. In addition we have found that an unsubstituted phenyl moiety in the acyl group represented by R is substituted by chlorine in the para position when using sulfuryl chloride both as reactant and as solvent.

Alternatively, certain compounds of the formula 1 may also be prepared by treating a 3,3-disubstituted cepham derivative of the formula 4 in which R, $R^1$, $R^2$, and $R^3$ are as defined above and Z is Cl, Br, or I with a halogenating agent such as a very large molar excess of sulfuryl chloride to obtain the corresponding compounds of formula 1 in which R, $R^1$, $R^2$, $R^3$, and Z are as defined above, $R^4$ is SCl, X is OH, and Y is Cl.

Furthermore we have found that treatment of the compounds of formula 1 obtained as described above with triethylamine, in the same manner as described by Kukolja et al. cited above for compounds of formula 1 in which $R^3$ and $R^4$ were both hydrogen, did not give the expected smooth reaction to yield the corresponding compounds of formula 2A, but that a mixture containing a multitude of compounds was obtained.

However, when treating the compounds of formula 1 obtained as described above with pyridine we obtained the corresponding compounds of formula 2A in the form of their single geometric isomer in which the substituent $R^4$ is trans to the carboxylic acid ester moiety. On the other hand, when treating the compounds of formula 1 obtained as described above with aniline we obtained the corresponding compounds of formula 2A in the form of their single geometric isomer in which the substituent $R^4$ is cis to the carboxylic acid ester moiety. In both the above geometric isomers of the compounds of formula 2A the meanings of R, $R^1$, $R^2$, $R^3$ and $R^4$ are as defined above, X is OH, and Y is a chlorine atom trans to the group RC(X)=N.

We have also found that treatment of the 2-(substituted methyl)penicillins of formula 3b in which X represents H, R, $R^1$ and $R^2$ are defined as above and $R^3$ and $R^4$ are both hydrogen with a very large molar excess of sulfuryl chloride used both as reactant and as solvent gives smoothly the corresponding compounds of formula 2A. If the starting material contains an unsubstituted phenyl moiety in the acyl group represented by R the latter will be substituted by chlorine in the para position. Furthermore, when treating a compound of formula 2A obtained as described in this paragraph with an N-haloimide such as N-bromo- or N-chloro-succinimide or with an N-haloamide such as N-bromo- or N-chloroacetamide there are obtained the corresponding compounds of formula 2A in which $R^3$ and $R^4$ are both the same, i.e., either both Br or both Cl. Also, when the acylamido group R C(OH)=N, i.e. RCONH, contains a free hydrogen atom in a methylene group adjacent to the carbonyl, said hydrogen atom will be replaced by the corresponding halogen when treating with an N-haloimide or an N-haloamide.

When it is desired to obtain compounds of formula 2B, i.e., the stereoisomers of the compounds of formula 2A in which the substituent Y is cis to the group RC(X)=N, we have found that it is advantageous to treat an unsym - azetidinone disulfide of the formula 5, prepared according to the method described by Kamiya et al. in Tetrahedron Letters 1973, 3001, in which R, $R^1$, $R^2$, $R^3$, and $R^4$ are as defined above, X is OH and $R^6$ is 2-benzothiazolyl or 2-benzoxazolyl, with a halogenating agent as defined above, preferably with a large molar excess of sulfuryl chloride. In this manner there are obtained the corresponding compounds of formula 2B in which R, $R^1$, $R^2$, $R^3$, and $R^4$ are as defined above, X is OH, and Y is a chlorine atom cis to the group RC(X)=N.

Furthermore, when the acyl group represented by R in the starting material of formula 5 contains an unsubstituted phenyl group, said latter group will be substituted by chlorine in the para position under the conditions of the above reaction.

The compounds of formula 2B in which either $R^3$ or $R^4$, or both $R^3$ and $R^4$ are hydrogen may be treated with an N-haloimide such as N- bromo- or N-chlorosuccinimide, or with an N-haloamide such as N-bromo- or N-chloroacetamide, to obtain the corresponding compounds of formula 2B in which $R^3$ or $R^4$, or both $R^3$ and $R^4$ are bromine or chlorine, respectively. Generally, mono-halogenated compounds of formula 2B are obtained when using one equivalent of haloimide or haloamide, and dihalogenated compounds are obtained when using two equivalents of haloimide or haloamide. However, when using as starting material a compound of formula 2B in which $R^3$ and $R^4$ are both hydrogen and in which the acylamido group represented by RC(OH)=N, i.e. RCONH, contains a free hydrogen atom in a methylene group adjacent to the carbonyl, and using 3 equivalents of an N-haloimide or N-haloamide, said hydrogen atom together with $R^3$ and $R^4$ will be replaced by the corresponding halogen.

The compounds of formula 2A and 2B are useful as intermediates in the synthesis of 1-oxacephalosporins, e.g. as described in U.S. Pat. No. 4,013,653, issued March 22, 1977.

For example, a compound of formula 2A or 2B in which RC(X)=N represents the phthalimido group, $R^1$ is methyl, $R^2$ and $R^3$ are hydrogen, $R^4$ is bromine, and Y is chlorine is treated with tetramethylguanidinium formate to obtain the corresponding compound of formula 2A or 2B in which $R^4$ is OCHO; hydrolysis of the latter formate ester, purification of the corresponding compound of formula 2A or 2B in which $R^4$ is OH by means of forming the tetrahydropyranyl ether thereof and purifying the latter, and treating the purified compound of formula 2A or 2B in which $R^4$ is OH with stannous chloride gives the corresponding 1-oxa-3-methyl-cephem.

It will be obvious to those skilled in the art that the nature of the groups represented by R and $R^1$ is immaterial for the process of this invention, and numerous examples of different groups R and $R^1$ are described in the literature, e.g. in U.S. Patents 4,009,159 and 3,989,685. Compounds in which the substituent $R^2$ is methoxy are described e.g. in Chem. Abs. 76, 99685f and ibid.77, 126661z, and by Koppel et al., J. Am.Chem. Soc. 95,2403(1973). The substituents $R^3$ and/or $R^4$ have been described as halogen or as an acyloxy group, e.g. by Wolfe et al. in Can. J. Chem 50, 2898(1972), and such substituents may be transformed into other substituents $R^3$ and/or $R^4$ as defined above by conventional means which are well known in the art. Numerous compounds in which X is OH or H are well known, and compounds similar to those of formula 1 in which X is SCl or SBr are described in British patent No. 1,523,885 issued from British application 16582/75. cited above which also describes the transformation of those latter substituents into other groups as defined above. Compounds in which Y is a halogen have been described e.g. by Wolfe et al. cited above, and compounds of formula 4 in which Z is a halogen have been described e.g. in "α-Lactam Antibiotics", J. Elks, Ed., Chemical Society, London 1977, Chapter 23. The transformation of such substituents Y and Z into other groups as defined above may also be carried out by conventional means.

DETAILED DESCRIPTION OF THE INVENTION

A 2-(substituted methyl)penicillin of the formula 3a in which R, $R^1$, and $R^2$ are as defined above, X is OH, $R^3$ is hydrogen and $R^4$ is a halogen selected from chlorine, bromine, and iodine, or an acyloxy group selected from formyloxy and acetoxy, for example a compound prepared as described in "β-Lactam Antibiotics", cited above, is dissolved in a suitable solvent and treated with a halogenating agent as defined above, preferably chlorine or sulfuryl chloride. Suitable solvents are inert to halogenating agents as defined above such as e.g. halogenated hydrocarbons containing from 1-2 carbon atoms and from 2-4 atoms of chlorine or bromine, with methylene chloride being preferred. Alternatively, sulfuryl chloride itself may be used both as reactant and as solvent. When using sulfuryl chloride as the halogenating agent the molar proportion of sulfuryl chloride to starting material is at least 2, and it is preferred to use about 3 molar equivalents of sulfuryl chloride per mole of starting material whenever the latter is used in solution in a solvent; in this case it is also preferred to employ sulfuryl chloride dissolved in an inert solvent miscible with the solvent used for the starting material, preferably dissolved in a halogenated hydrocarbon such as defined above. A very large molar excess of sulfuryl chloride will obviously be used when employing sulfuryl chloride both as reactant and as solvent, for example about 3 parts by volume of sulfuryl chloride to about one part by weight of the starting material.

The temperature at which the above reaction is carried out may range from $-75°$ C. to room temperature, with a preferred range of from $-75°$ C. to $0°$ C. The time of the reaction may vary from 1-60 minutes, and it is generally preferred to use reaction times of from 1-5 minutes when using sulfuryl chloride both as reactant and as solvent, and to employ reaction times of from 5-60 minutes, preferably from 15-30 minutes when conducting the reaction in a solvent. During said latter period of time the reaction mixture is advantageously allowed to warm to $-20°$ C.$-0°$ C., preferably to about $-10°$ C.

The reaction is then quenched by addition of a lower alkanol containing water, preferably methanol or ethanol containing about 5% water, or the reaction mixture is washed with ice-cold brine. Washing with dilute aqueous sodium bicarbonate solution followed by washing with water and drying gives, upon evaporation of the solvent, the corresponding compound of formula 1. The same compound is also obtained when using about 3 molar equivalents of chlorine in solution in an inert solvent and working up as described above, or when using a very large molar excess of sulfuryl chloride both as reactant and as solvent, for example 3 parts by volume of sulfuryl chloride and one part by weight of the starting material. In the latter case it is preferred to add the solid starting material to ice-cold sulfuryl chloride with stirring, allowing the reaction to proceed for 1-2 minutes and evaporating excess sulfuryl chloride under reduced pressure, to obtain the corresponding compound of formula 1 as the residue. When conducting the above reaction with sulfuryl chloride in the absence of a solvent, i.e. when using a very large molar excess of sulfuryl chloride both as reactant and as solvent, we have also found that an unsubstituted phenyl group in the acylamido group RCONH will be substituted with chlorine in the para position at the same time. For example, when starting with a compound of the formula 3a in which RCONH represents the phenoxyacetamido group and proceeding as above using a very large molar excess of sulfuryl chloride both as reactant and as solvent, the compound of formula 1 which is obtained after working up as described above contains the p-chlorophenoxy-acetamido moiety as the group RCONH.

The preferred starting materials for the above reaction step are the 2-(substituted methyl)penicillins of the formula 3a as described above. However, we have also found that certain 3,3-disubstituted cepham derivatives, for example the compounds of formula 4 in which X is OH and Z represents chlorine, bromine, or iodine are equally useful starting materials. The process of treating with the halogenating agent, e.g. sulfuryl chloride or chlorine, is carried out exactly in the same manner as described above and working up of the reaction mixture is also done in the same manner. We have found again that an unsubstituted phenyl group in the acylamido group RCONH will be chlorinated in the para position when using a very large molar excess of sulfuryl chloride both as reactant and as solvent, so that e.g. a phenoxyacetamido group in the starting material of formula 4 will become a p-chlorophenoxyacetamido group in the compound of formula 1 obtained in the above reaction.

The compounds of formula 1 obtained as described above from a 2-(substituted methyl)penicillin are azetidinone derivatives in which $R^1$, $R^2$, $R^3$, and $R^4$ are the same as defined in the starting material; the substituent R is also the same as in the starting material except for possible chlorination in the para position as discussed above; X is OH; Y is chlorine; Z is SCl; when a 3,3-disubstituted cepham derivative as defined above is used as the starting material the compounds of formula 1 are obtained in which $R^1$, $R^2$, $R^3$, X, Y, and Z are the same as the starting material, R is also the same as in the starting material except for possible chlorination as discussed above, and $R^4$ is SCl. In both cases the compounds of formula 1 are obtained as the single stereoisomer in which the substituent Y is trans to the group RC(X)=N. The above reaction step yields the compounds of formula 1 in a sufficiently pure state so that they may be used in the subsequent reaction step without further purification.

The compounds of formula 1 obtained as described above are treated with an organic base selected from heterocyclic nitrogen bases containing from 4-5 carbon atoms and from 1-2 nitrogen atoms, and from aromatic amines containing a phenyl ring and one or two nitrogen atoms, to yield the corresponding compounds of formula 2A. Preferred bases for the above reaction are pyridine and aniline. The reaction may be carried out in the absence of a solvent, with the appropriate base being used both as reactant and as solvent, or with the use of an inert solvent, preferably a halogenated hydrocarbon as defined above; deuterochloroform is particularly advantageous in the latter case because it permits monitoring the progress of the reaction by nmr spectroscopy under experimental conditions, but chloroform is obviously the solvent of choice when it is advantageous to use a solvent. The reaction is carried out at temperatures within the range of 0°-30° C., preferably at about 25° C., for periods of time of from 1-15 minutes, preferably for about 5 minutes, using at least two molar equivalents of the base per mole of starting material, and a very large molar excess of the base when the latter is used both as reactant and as solvent, for example 3 parts by volume of the base for 1-2 parts by weight of the starting material. Excess base and/or solvent are removed under reduced pressure and the residue is taken up in a halogenated hydrocarbon solvent as defined above, or the reaction mixture is taken up in a halogenated hydrocarbon solvent as described above. Washing with dilute hydrochloric acid and water, drying, and evaporation of the solvent yields the corresponding unsaturated azetidinone derivative of formula 2A in which R, $R^1$, $R^2$, $R^3$, $R^4$, X and Y are the same as in the starting material of formula 1, and in the form of the single stereoisomer in which the substituent Y, e.g. chlorine, is trans to the group RC(X)=N.

However, we have also found that the nature of the base has a profound influence upon the outcome of the above reaction. For example, when using pyridine as the base the compound of formula 2A obtained as described above will be in the form of its single geometric isomer in which the substituent $R^4$ is trans to the carboxylic acid ester moiety, and when using aniline as the base the compound of formula 2A will be obtained as its single geometric isomer in which the substituent $R^4$ is cis to the carboxylic acid ester moiety, both as evidenced by nmr spectroscopy.

The compounds of formula 2A prepared as described above are generally obtained in a sufficiently pure state to be used without further purification in subsequent reactions. However, it may sometimes be advantageous to purify the compounds of formula 2A by rapid chromatography on silica gel with mixtures of ether and methylene chloride as the eluants.

Alternatively, certain compounds of formula 2A, in particular those in which X is H(Schiff bases) and $R^3$ and $R^4$ are both hydrogen, may also be prepared by treating the corresponding starting material of formula 3b in which X, $R^3$, and $R^4$ are all hydrogen, with a very large molar excess of sulfuryl chloride used both as reactant and as solvent. The reaction is advantageously carried out at temperatures in the range of $-40°$ C. to 30° C., preferably in the range of $-10°$ C. to 10° C., and the reaction mixture is worked up as described above to yield the corresponding compound of formula 2A in which R, $R^1$, $R^2$, $R^3$, $R^4$, and X are the same as in the starting material and Y is chlorine, except that when R in the starting material represents an unsubstituted phenyl group the latter will be chlorinated in the para position. The above compounds of formula 2A are again obtained in the form of their single stereoisomer in which the substituent Y, e.g. chlorine, is trans to the group RC(X)=N.

When it is desired to obtain compounds of the formula 2B we have found that this may be accomplished advantageously by treating an unsym-azetidinone disulfide of the formula 5 with sulfuryl chloride. The starting material of formula 5 in which R, $R^1$, $R^2$, $R^3$, and $R^4$ are as defined in the first instance, X is OH, and $R^6$ is 2-benzothiazolyl or 2-benzoxazolyl are dissolved in a halogenated hydrocarbon solvent as defined above, and treated with a very large molar excess of sulfuryl chloride. The temperature of the reaction is held within the range of from $-75°-0°$ C., preferably at about $-75°$ C., for 5-60 minutes, preferably for about 30 minutes, and then at ambient temperature for another 5-60 minutes, preferably for about 30 minutes, with constant agitation. Washing with aqueous sodium bicarbonate and with brine, drying, and evaporation of the solvent yields the corresponding compound of formula 2B in which R, $R^1$, $R^2$, $R^3$, $R^4$, and X are as defined in the starting material and Y is chlorine. The compounds of formula 2B prepared as above are obtained in the form of their single stereoisomer in which the substituent Y (chlorine) is cis to the group RC(X)=N. Furthermore, when R in the starting material represents an unsubstituted phenyl group the latter will again be chlorinated in the para position, as described above.

The starting materials for the above reactions are known compounds or are prepared by know procedures. Thus, the compounds of formulae 3a and 3b are prepared as described e.g. in "β-Lactam Antibiotics" cited above, or by T. Jen et al. in J. Org. Chem. 38, 2857 (1973); The compounds of formula 4 are prepared according to the methods described in "β-Lactam Antibiotics", cited above; and the compounds of formula 5 are prepared as described by Kamiya et al. in Tetrahedron Letters 1973, 3001.

Certain compounds of formula 2B, in particular those in which $R^3$ and/or $R^4$ are hydrogen, may be further substituted by subjecting them to the appropriate reaction conditions. For example, such compounds may be treated with an N-haloimide such as N-chloro- or N-bromosuccinimide, or with an N-haloamide such as N-chloro or N-bromoacetamide, in solution in an inert solvent such as a halogenated hydrocarbon as defined above, preferably carbon tetrachloride, and in the presence of small amounts of a free radical generator, for example benzoyl peroxide, preferably with the use of radiant energy such as supplied e.g. by an incandescent lamp. The reaction is carried out at temperatures above room temperature and preferably at or near the boiling point of the reaction mixture for periods of time of from 10-60 minutes, preferably for about 30 minutes. Filtration of the reaction mixture, contacting the filtrate with ice-cold sodium bisulfite in aqueous solution, extraction with a water-immiscible solvent such as a halogenated hydrocarbon as defined above, preferably methylene chloride, washing of the organic phase with brine, drying, and evaporation of the solvent yields the corresponding compound of formula 2B in which R, $R^1$, $R^2$, X and Y are the same as defined in the starting material and $R^3$ and/or $R^4$ are chlorine or bromine, depending upon the haloimide or haloamide used. The quantities of the latter determine the result of the reaction. When one equivalent of haloimide or haloamide is used only $R^3$ or $R^4$ will be halogen (chlorine or bromine) in the final product. When two equivalents are used both $R^3$ and $R^4$ are chlorine or bromine, respectively. However, when three equivalents of haloimide or haloamide are used and when the substituent R in the starting material contains a free methylene group adjacent to the carbonyl group, one of the hydrogen atoms in said free methylene group is also replaced by halogen (chlorine or bromine) in the course of the above reaction. For example, when the group RCONH in the starting material represents the p-chlorophenoxyacetamido moiety the latter is transformed to the p-chlorophenoxy-α-bromoacetamido group when using three equivalents of N-bromosuccinimide in the above reaction.

The following formulae and Examples will illustrate the above invention; the Examples are given for illustrative purposes only and do not in any way limit the scope of this invention.

EXAMPLE 1

2,2,2-Trichloroethyl 3S-Phenoxyacetamido-4S(trans)-chloroazetidinone-1-α(β-chloromethyl-β-sulfenylchloride)butyrate(1, R=$C_6H_5OCH_2$, $R^1$=$CH_2CCl_3$, $R^2$=$R^3$=H, $R^4$=Cl, X=OH, Y=Cl, Z=SCl)

2,2,2-Trichloroethyl 6-phenoxyacetamido-2-chloromethyl-2-methylpenam-3-carboxylate (3a, R=$C_6H_5OCH_2$, $R^1$=$CH_2CCL_3$, $R^2$=$R^3$=H, $R^4$=Cl, X=OH, 1.03 g., 2 mmole) was dissolved in methylene chloride (15 ml) and the solution stirred and cooled to −75° C. Sulfuryl chloride (19.5 ml of a solution in methylene chloride containing 41.6 mg per ml—0.81 g., 6 mmole) cooled to −75° C. was added slowly and the mixture stirred for 20 mins. Methanol (containing 5% water—7.7 ml of a solution in methylene chloride containing 32 mg/ml—0.224 g., 7.2 mmole) was then added at −75° C., and the mixture allowed to warm to −10° C., washed with cold brine, then aqueous sodium bicarbonate, then cold water, and dried (MgSO$_4$). After filtration and concentration of the reaction mixture 1.1 g (94%) of the title compound in the form of a light yellow foam was obtained. The pmr (CDCL$_3$) spectrum:δ1.8 (s, 3H, C$\underline{H}_3$), 4.12 (s, 2H, C$\underline{H}_2$Cl), 4.48 (s, 2H, C$\underline{H}_2$CCl$_3$), 4.8 (s, 2H, OC$\underline{H}_2$), 4.88 (s, 1H, C$\underline{H}$COOCH$_2$CCl$_3$), 5.0(dd, 1H, C$_3$—$\underline{H}$), 5.8 (d, J=2 c/s, 1H, C$_4$—$\underline{H}$), 6.78 to 7.4 (m, 6H, C$_6\underline{H}_5$ and N$\underline{H}$) was characteristic of a compound of formula 1, the splitting of the C$_3$ and C$_4$ β-lactam protons (J=2 c/s) being characteristic of the trans-isomer. There was no indication in the pmr spectra (in CDCl$_3$, C$_6$D$_6$ or acetone d$_6$) of the crude material of the presence of the possible cis-isomer.

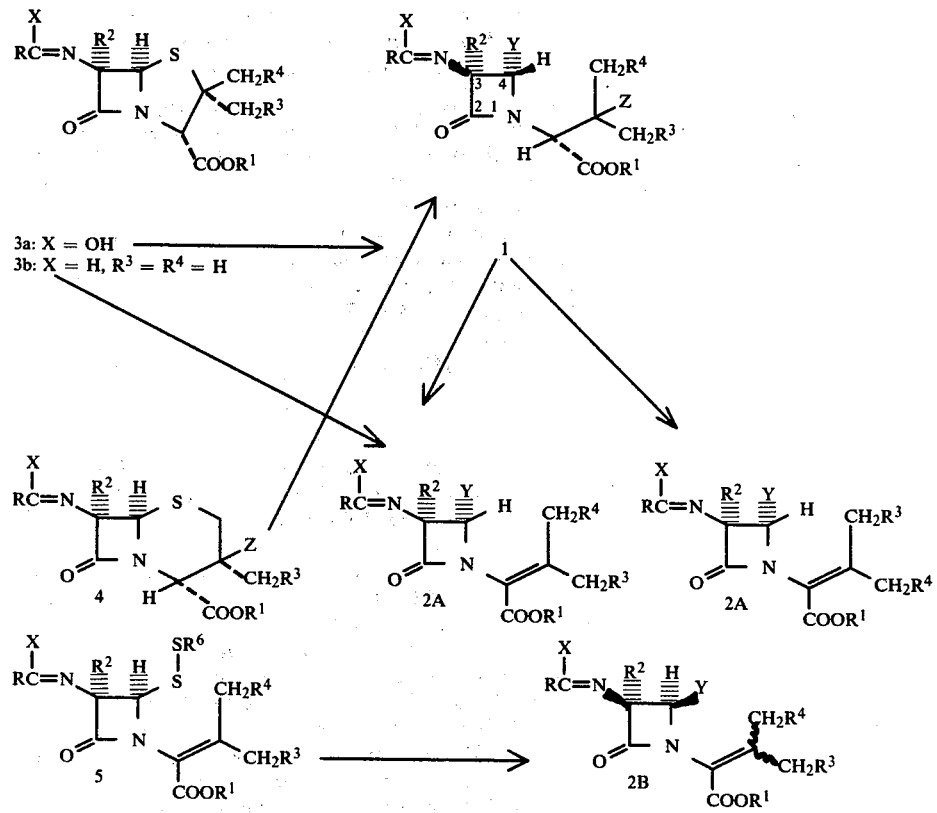

When the reaction was repeated using one equivalent of sulfuryl chloride only about 5% reaction took place, about 50% starting penicillin being recovered.

Aqueous ethanol could be used instead of aqueous methanol in the work up, with the same results. When the addition of the alcohol was omitted, under otherwise identical conditions (using 3 equivalents of sulfuryl chloride) but washing first with aqueous sodium bicarbonate, the product showed the presence of about 50% of the starting penicillin. If however both the alcohol and aqueous bicarbonate washes were omitted, and the crude reaction product (using 3 equivalents of sulfuryl chloride) was washed with cold brine, the nmr spectrum of the product indicated complete reaction to give the title compound.

Increasing the amount of sulfuryl chloride gave essentially the same reaction, except that with very large amounts of sulfuryl chloride chlorination of the phenyl group in the para-position also occurred. This reaction was best done by using sulfuryl chloride as reagent and solvent (see Example 3).

The title compound is very difficult to purify, but the procedure described above provides a product of sufficient purity for further reactions.

EXAMPLE 2

2,2,2-Trichloroethyl 3S-Phenoxyacetamido-4S(trans)-chloroazetidinone-1-α(β-chloromethyl-β-sulfenylchloride)butyrate(1, R=$C_6H_5OCH_2$, $R^1$=$CH_2CCl_3$, $R^2$=$R^3$=H, $R^4$=Cl, X=OH, Y=Cl, Z=SCl).

2,2,2-Trichloroethyl 6-phenoxyacetamido-2-chloromethyl-2-methylpenam-3-carboxylate (3a, R=$C_6H_5OCH_2$, $R^1$=$CH_2CCl_3$, $R^2$=$R^3$=H, $R^4$=Cl, X=OH, 0.206 g., 0.4 mmole) was dissolved in methylene chloride (2 ml) and the solution stirred and cooled to −75° C. A solution of chlorine in methylene chloride (1.14 ml of a solution containing 75 mg chlorine per ml., 95 mg., 1.2 mmole) was added at −75° C. and the reaction mixture was stirred for 15 mins. Methanol in methylene chloride (1.6 ml of a solution containing 29 mg of 95% methanol per ml., 46 mg., 1.44 mmole) was added and the stirred mixture allowed to warm to −10° over a 20 min. period. Work up as described in Example 1 gave a 100% yield of the title compound, i.e., the same product as described in Example 1 with the same pmr spectrum.

EXAMPLE 3

2,2,2-Trichloroethyl 3S-p-Chlorophenoxyacetamido-4S(trans)-chloroazetidinone-1-α(β-chloromethyl-β-sulfenylchloride)butyrate, (1,R=p-ClC$_6$H$_4$OCH$_2$, $R^1$=$CH_2CCl_3$, $R^2$=$R^3$=H, $R^4$=Cl, X=OH, Y=Cl, Z=SCl).

2,2,2-Trichloroethyl 6-phenoxyacetamido-2-chloromethyl-2-methylpenam-3-carboxylate (3a, R=$C_6H_5OCH_2$, $R^1$=$CH_2CCl_3$, $R^2$=$R^3$=H, $R^4$=Cl, X=OH, 2.0 g., 3.88 mmoles) was added to stirred ice-cold sulfuryl chloride (6 ml). After one minute the reaction solution was concentrated under reduced pressure to give a yellowish foam. The foam was dissolved in ether and the compound precipitated at −75° C. using hexane. An almost white amorphous solid, 2.35 g (100%) was obtained. The pmr (CDCl$_3$) spectrum was almost the same as that of the compound from Example 1, except that the phenyl signals appeared as a four proton AB type quartet as δ6.85 and 7.3, characteristic of a p-disubstituted phenyl group.

EXAMPLE 4

2,2,2-Trichloroethyl 3S-Phenoxyacetamido-4S(trans)-chloroazetidinone-1-α(β-bromomethyl-β-sulfenylchloride)butyrate (1, R=$C_6H_5OCH_2$, $R^1$=$CH_2CCl_3$, $R^2$=$R^3$=H, $R^4$=Br, X=OH, Y=Cl, Z=SCl).

2,2,2-Trichloroethyl 6-phenoxyacetamido-2-bromomethyl-2-methylpenam-3-carboxylate (3a,R=$C_6H_5OCH_2$, $R^1$=$CH_2CCl_3$, $R^2$=$R^3$=H, $R^4$=Br, X=OH, 3.1 g., 5.5 mmoles) was dissolved in methylene chloride (30 ml) and the resulting solution cooled to −75° C. A solution of sulfuryl chloride in methylene chloride (2.23 g., in 30 ml methylene chloride, 15.5 mmoles) cooled to −75° C. was added and the mixture stirred for 15 mins. A solution of 95% methanol in methylene chloride (21 ml of a solution containing 32 mg. per ml., 640 mg., 20 mmole) was added at −75° C. and the mixture allowed to warm to −10° C. The reaction mixture was washed with cold brine, and dried (MgSO$_4$), filtered, and concentrated to give 3.19 g. (92%) of the title compound as a yellow foam. The pmr (CDCl$_3$) spectrum: δ1.88 (s, 3H,C$\underline{H}_3$), 4.17 (s, 2H, C$\underline{H}_2$Br), 4.55 (s, 2H, C$\underline{H}_2$CCl$_3$), 4.88 (d, 3H, —OC$\underline{H}_2$— and C$\underline{H}$COOCH$_2$CCl$_3$), 5.00 (dd, 1H, C$_3$—$\underline{H}$), 5.9 (d, J=2 c/s, 1H, C$_4$—$\underline{H}$), 6.88 to 7.60 (m, 6H, C$_6\underline{H}_5$ and N$\underline{H}$) is characteristic of this compound. Again there was no evidence in the pmr spectrum of the possible cis-isomer.

EXAMPLE 5

2,2,2-Trichloroethyl 3S-Phenoxyacetamido-4S(trans)-chloroazetidinone-1-α(β-iodomethyl-β-sulfenylchloride)butyrate (1, R=$C_6H_5OCH_2$, $R^1$=$CH_2CCl_3$, $R^2$=$R^3$=H, $R^4$=I, X=OH, Y=Cl, Z=SC1).

When a sample of 2,2,2-trichloroethyl 6-phenoxyacetamido-2-iodomethyl-2-methylpenam-3-carboxylate (3a,R=$C_6H_5OCH_2$, $R^1$=$CH_2CCl_3$, $R^2$=$R^3$=H, $R^4$=I, X=OH), was treated with sulfuryl chloride (3 equivalents) in methylene chloride at −75° C., by the same procedure as described in Examples 1 and 4, the title compound was obtained and characterized by its pmr spectrum (CDCL$_3$) δ2.13(s, 3H, —C$\underline{H}_3$), 3.85 (s, 2H, —C$\underline{H}_2$I), 4.43 (s, 2H, —C$\underline{H}_2$CCl$_3$), 4.93–4.73 (m, 4H, —OC$\underline{H}_2$, —C$\underline{H}$COO, and C$_3$—$\underline{H}$), 5.73 (d, J=2 Hz, 1H, C$_4$—$\underline{H}$), 7.43–6.73 (m, 5H, aryl and N$\underline{H}$).

EXAMPLE 6

Methyl 3S-Phenoxyacetamido-4S(trans)-chloroazetidinone-1-α(β-acetoxymethyl-β-sulfenylchloride)butyrate, (1, R=$C_6H_5OCH_2$, $R^1$=CH$_3$, $R^2$=$R^3$=H, $R^4$=OCOCH$_3$, X=OH, Y=Cl, Z=SCl)

A solution of the 2β-acetoxymethylpenam derivative (3a, R=$C_6H_5OCH_2$, $R^1$=CH$_3$, $R^2$=$R^3$=H, $R^4$=OCOCH$_3$, X=OH, 211 mg, 0.5 mmole) in methylene chloride (5 ml) was cooled to −75° C. and sulfuryl chloride (202.5 mg, 1.5 mmole) was added dropwise with stirring which was continued for 15 minutes. Methanol (95%, 55.8 mg, 1.8 mmole, 70μl) was added and the mixture was allowed to warm to −10° C. It was washed with cold saturated sodium bicarbonate solution until neutral, then washed with water and brine, dried, and evaporated, to give the title compound as a yellow foam in 73% yield with nmr (CDCl$_3$), δ1.68(s, 3H, —CH$_3$), 2.10(s, 3H, —CO—CH$_3$), 3.81 (s, 3H, —OCH$_3$), 4.50 (m,2H, —CH$_2$OAc),4.53(s, 2H, —OCH$_2$CO—), 4.67(s, 1H), 5.00 (dd, J=1.5 Hz, 8 Hz, 1H, β-lactam), 5.80 (d, J=1.5 Hz, 1H, β-lactam), 6.67 to 7.67 (m, 6H, amide and aromatic protons).

When the same reaction was carried out at 0° C. the resulting product was the corresponding p-chlorophenoxyacetamido derivative as evidenced by its nmr spectrum.

In the same manner as described in any one of Example 1–6 inclusive, when using the methyl, ethyl, propyl, isopropyl, t-butyl, trichloroethyl, benzyl, p-nitrobenzyl, or benzhydryl esters of 6-phenylacetamido-, 6-(2-thienylacetamido)-, 6-(tetrazolyl-1-acetamido)-, or 6-(3-phenyl-5-methylisoxazol-4-carbamido)-2-chloro-, 2-bromo, 2-iodo, 2-formyloxy-, or 2-acetoxy-2-methylpenam-3-carboxylic acid as starting materials, and when using chlorine, sulfuryl chloride, bromine or sulfuryl bromide as the halogenating agent, the corresponding methyl, ethyl, propyl, isopropyl, t-butyl, trichloroethyl, benzyl, p-nitrobenzyl, or benzhydryl esters of 3S-phenylacetamido-, 3S-(2-thienylacetamido)-, 3S-(tetrazolyl-1-acetamido)- or 3S-(3-phenyl-5-methylisoxazol-4-carbamido)-4S(trans)chloro- or 4S(trans)-bromoazetidinone-1-α(β-chloromethyl-, β-bromomethyl-, β-iodomethyl-, β-formyloxymethyl- or β-acetoxymethyl-β-sulfenylchloride or β-sulfenylbromide)butyric acid are obtained, respectively.

EXAMPLE 7

2,2,2-Trichloroethyl 3S-Phenoxyacetamido-4S(trans)-chloroazetidinone-1-(3′-chloromethylbut-2′-enoate) (trans-isomer) (2A, R=C$_6$H$_5$OCH$_2$, R$^1$=CH$_2$CCl$_3$, R$^2$=R$^3$=H, R$^4$=Cl, X=OH, Y=Cl).

The compound of formula 1,2,2,2-trichloroethyl 3S-phenoxyacetamido-4S(trans)chloroazetidinone-1α(β-chloromethyl-β-sulfenylchloride)butyrate obtained as described in Examples 1 or 2, (1.1 g., 2 mmoles) was dissolved in pyridine (3 ml) at room temperature and stirred for 5 minutes, then concentrated under reduced pressure. The residue was taken up in methylene chloride, washed with dilute hydrochloric acid, then water, dried (MgSO$_4$), and the filtrate concentrated, when 1.0 g. (96%) of the title compound was obtained as an off white foam. The pmr spectrum (CDCl$_3$), δ2.58 (s, 3H, CH$_3$), 4.4 (ABq, 2H, CH$_2$Cl), 4.6 (s, 2H, CH$_2$CCl$_2$), 4.9 (s, 2H, O—CH$_2$—), 5.18 (dd, 1H, C$_3$—H), 6.12 (d, J=2 c/s, 1H, C$_4$—H), 6.9 to 7.65 (m, 6H, C$_6$H$_5$ and NH), was in agreement with the structure of the geometric isomer in which the CH$_2$Cl group is trans to the ester group, and also showed no trace of the other geometric isomer in which the CH$_2$Cl group is cis-to the ester group. The structural assignment was made on the basis of the pmr spectrum, which showed that only one isomer is obtained by this process. The product as obtained was pure enough for further reactions. It could be purified further by rapid chromatography through a silica column using ether-methylene chloride as eluant.

EXAMPLE 8

2,2,2-Trichloroethyl 3-S-Phenoxyacetamido-4S(trans)-chloroazetidinone-1-(3′-chloromethylbut-2′-enoate) (cis-isomer) (2A,R=C$_6$H$_5$OCH$_2$, R$^1$=CH$_2$CCl$_3$, R$^2$=R$^3$=H, R$^4$=Cl, X=OH, Y=Cl).

A solution of 2,2,2-trichloroethyl 3S-phenoxyacetamido-4S(trans)-chloroazetidinone-1-α(β-chloromethyl-β-sulfenyl chloride)butyrate (1, R=C$_6$H$_5$OCH$_2$, R$^1$=CH$_2$CCl$_3$, R$^2$=R$^3$=H, R$^4$=Cl, X=OH, Y=Cl, Z=SCl, (623 mg., 1 mmole) obtained as described in Examples 1 or 2 was dissolved in deuterochloroform (1 ml) and aniline (2 mmoles) added, the reaction being monitored by pmr spectroscopy. The reaction mixture was washed with dilute hydrochloric acid and water, dried (MgSO$_4$), filtered and concentrated when a foam resulted. The foam was taken up in ether and precipitated with hexane at −75° C. to give 560 mg of a beige solid whose pmr (CDCl$_3$) spectrum was very similar to that of the product of Example 7 and was in agreement with the assigned structure except that the CH$_3$ singlet appeared at δ1.62 indicating that the CH$_2$Cl group was cis to the ester group COOCH$_2$CCl$_3$.

EXAMPLE 9

2,2,2-Trichloroethyl 3S-Phenoxyacetamido-4S(trans)-chloroazetidinone-1-(3′-bromomethylbut-2′-enoate) (trans-isomer) (2A, R=C$_6$H$_5$OCH$_2$, R$^1$=CH$_2$CCl$_3$, R$^2$=R$^3$=H, R$^4$=Br, X=OH, Y=Cl).

The compound of formula 1 obtained as described in Example 4 (1.89 g., 3 mmole) was stirred with ice-cold pyridine (3 ml) for 5 mins. and cold hexane then added and the crude product separated by decantation. The product was taken up in methylene chloride, the solution washed with ice water, dried (MgSO$_4$), filtered and concentrated to give 1.13 g. (67%) of the title compound as a red foam. The pmr (CDCl$_3$) spectrum: δ2.50 (s, 3H, CH$_3$), 4.25 (Abq, 2H, CH$_2$Br), 4.6 (s, 2H, CH$_2$CCl$_3$), 4.9 (s, 2H, —OCH$_2$—), 5.15 (dd, 1H, C$_3$—H), 6.15 (d, J=2 c/s, 1H, C$_4$—H), 6.85 to 7.5 (m, 6H, C$_6$H$_5$ and NH), is in agreement with the assignment showing the CH$_2$Br group trans to the ester group COOCH$_2$CCl$_3$.

EXAMPLE 10

Methyl 3-S-p-Chlorobenzalamino-4S(trans)-chloroazetidinone-1-α-propenylacetate (2A, R=p-ClC$_6$H$_4$, R$^1$=CH$_3$, R$^2$=R$^3$=R$^4$=H, X=H, Y=Cl).

Methyl 6-benzalamino-2, 2-dimethylpenam-3-carboxylate,(3b, R=C$_6$H$_5$, R$^1$=CH$_3$, R$^2$=R$^3$=R$^4$=H, X=H, 0.5 g.) was dissolved in ice-cold sulfuryl chloride (3 ml) and the reaction followed at about 0° C. by the pmr spectrum. There was an immediate reaction with gas evolution and the pmr (SO$_2$Cl$_2$) spectrum immediately after solution—δ1.9 and 2.1 (ss, 6H, gem-CH$_3$), 3.62 (s, 3H, COOCH$_3$), 5.42 and 6.45 (ss, 2H, β-lactam trans-protons), 7.5 and 8.3 (ABq, 4H, C$_6$H$_4$), 8.9 (s, 1H, φCH=)—showed complete conversion to the title compound.

EXAMPLE 11

2,2,2-Trichloroethyl 3-S-p-Chlorophenoxyacetamido-4-R(cis)chloroazetidinone-1-α-propenylacetate (2B,R=p-ClC$_6$H$_4$OCH$_2$, R$^1$=CH$_2$CCl$_3$, R$^2$=R$^3$=R$^4$=H, X=OH, Y=Cl).

Trichloroethyl 3-S-phenoxyacetamido-4-S-(2-benzothiazole disulfide)azetidinone 1-α-propenylacetate (5, R=C$_6$H$_5$OCH$_2$, R$^1$=CH$_2$CCl$_3$, R$^2$=R$^3$=R$^4$=H, R$^6$=2-benzothiazolyl, X=OH, 3.25 g., 5 mmoles) was dissolved in methylene chloride (25 ml) and the solution cooled to −75° C. Sulfuryl chloride (3 ml) was added, and the reaction mixture stirred at this temperature for 30 mins. and at ambient temperature for 30 mins. The resulting solution was diluted with ether and the resulting precipitate removed by filtration. The filtrate was washed with ice-cold, saturated, aqueous sodium bicarbonate, then brine, and dried (MgSO$_4$). Filtration and concentration gave the title compound as an oil. Chromatography on silica gel using benzene followed by benzene with 10% ethyl acetate, gave 1.793 g. (69%) of the title compound as a white foam. The pmr (CDCl$_3$) spectrum, $\delta$2.17 and 2.42 (ss, 6H, gem-C$\underline{H}_3$), 4.59 (s, 2H, —OC$\underline{H}_2$—), 4.75 and 4.85 (ss, 2H, C$\underline{H}_2$CCl$_3$), 5.6 and 5.73 (dd, J=5 c/s, 1H, C$_3$-$\underline{H}$), 6.20 (d, J=5 c/s, 1H, C$_4$-$\underline{H}$), 6.9 and 7.28 (ABq, 4H, C$_6\underline{H}_4$), 7.68 (d, 1H, N$\underline{H}$), is in agreement with the assigned structure and the splitting constant (J=5 c/s) of the $\beta$-lactam protons shows that these protons are cis- to each other as indicated.

EXAMPLE 12

2,2,2-Trichlorethyl 3-S-p-Chlorophenoxy-$\alpha$-bromoacetamido-4-R(cis)-chloroazetidinone-1-Bis-(monobromoethyl)-$\alpha$-ethyleneacetate (2B, R=p-ClC$_6$H$_4$OCHBr, R$^1$=CH$_2$CCl$_3$, R$^2$=H, R$^3$=R$^4$=Br, X=OH, Y=Cl).

N-bromosuccinimide (2.16 g., 12 mmole) was added to a carbon tetrachloride (25 ml) solution of the compound of formula 2B obtained as described in Example 11 (1.793 g., 3.46 mmoles), a catalytic amount of benzoyl peroxide was introduced, the stirred mixture brought to reflux by heating and then maintained at reflux for 30 mins. by exposure to light (Sylvania No. 2 Superflood—115-120 V bulb). By this time the succinimide had separated from the reaction solution. The light brown solution was poured into ice and 5% sodium bisulfite and the mixture extracted with methylene chloride (2×50 ml). The combined organic layer was washed with saturated brine (twice), dried (MgSO$_4$), filtered and concentrated to give 2.894 g. (100%) of the title compound as a very pale brown foam. The pmr (CDCl$_3$) spectrum was in agreement with the proposed structure: the absence of the singlet due to the CH$_3$ protons proved that the product is indeed the bis(-bromomethyl) derivative.

EXAMPLE 13

Methyl 3-S-p-chlorophenoxyacetamido-4-S(trans)-chloroazetidinone-1-$\alpha$($\beta$-methylsulfenylchloride-$\beta$-chloro)butyrate (1, R=p-ClC$_6$H$_5$OCH$_2$, R$^1$=CH$_3$, R$^2$=R$^3$=H, R$^4$=SCl, X=OH, Y=Cl, Z=Cl).

When a sample of methyl 7-phenoxyacetamido-3-chloro-3-methylcepham-4-carboxylate (4, R=C$_6$H$_5$OCH$_2$, R$^1$=CH$_3$, R$^2$=R$^3$=H, X=OH, Z=Cl) was treated with sulfuryl chloride in the absence of a solvent in the same manner as described in Example 3 the title compound was obtained, as evidenced by the following spectrum: nmr(SO$_2$Cl$_2$) $\delta$1.73 (s, 3H, —CH$_3$), 3.00 (br s, 2H, CH$_2$SCl), 3.50 (s, 3H—CO$_2$CH$_3$), 4.17 (s, 2H, OCH$_2$—CO—), 4.30 (m, 1H, C$_3$—H), 4.67 (s, 1H, —CHCO$_2$—), 5.73 (d, J=2Hz, 1H), 6.57 6.97 (ABq, 2H, J=10Hz).

In the same manner as described above, but using sulfuryl bromide instead of sulfuryl chloride, there is obtained methyl 3-S-p-bromophenoxyacetamido-4-S(trans)-bromoazetidinone-1$\alpha$($\beta$-methylsulfenylbromide-$\beta$-chloro)butyrate.

EXAMPLE 14

Benzhydryl 3-S-Phenoxyacetamido-4-S(trans)-chloroazetidinone-1-$\alpha$($\beta$-methylsulfenylchloride-$\beta$-bromo)butyrate (1, R=p-ClC$_6$H$_4$OCH$_2$, R$^1$=CH$_3$(C$_6$H$_5$)$_2$, R$^2$=R$^3$=H, R$^4$=SCl, X=OH, Y=Cl, Z=Br).

Sulfuryl chloride (0.15 ml) was added to a solution of benzhydryl 7-phenoxyacetamido-3-bromo-3-methylcepham-4-carboxylate (4, R=C$_6$H$_5$OCH$_2$, R$^1$=HC(C$_6$H$_5$)$_2$, R$^2$=R$^3$=H, X=OH, Z=Br, 110 mg) in 1 ml. deuterochloroform. The mixture was shaken at room temperature and the reaction was followed by pmr spectroscopy. After one minute the reaction was complete and the title compound was obtained in substantially quantitative yield as the substantially pure 4-(trans)-chloro isomer with nmr(CDCl$_3$) $\delta$3.20 (s, 3H), 3.80 and 4.25 (ABq, 2H, J=16 Hz), 4.53 (m, 3H), 5.17 (s, 1H), 6.10 (d, J=2 Hz, 1H), 6.85 (s, 1H), 6.70 to 7.67 (m, for all aromatic protons).

In the same manner as described above, but using sulfuryl bromide instead of sulfuryl chloride, there is obtained benzhydryl 3-S-phenoxyacetamido-4-S(trans)-bromoazetidinone-1$\alpha$($\beta$-methylsulfenylbromide-$\beta$-bromo)butyrate.

EXAMPLE 15

Methyl 3-S-Phthalimido-4-S(trans)-chloroazetidinone-1-$\alpha$($\beta$-methylsulfenylchloride-$\beta$-chloro)butyrate (1, RC(X)=N=phthalimido, R$^1$=CH$_3$, R$^2$=R$^3$=H, R$^4$=SCl, Y=Cl, Z=Cl).

Methyl 7-phthalimido-3-chloro-3-methylcepham-4-carboxylate-(4, RC(X)=N=phthalimido, R$^1$=CH$_3$, R$^2$=R$^3$=H, Z=Cl, 60 mg) in solution in deuterochloroform was added at room temperature to sulfuryl chloride (0.1 ml) and the mixture was shaken for 2-3 minutes, to give the title compound substantially free from the 4-(cis)-chloro isomer in substantially quantitative yield, with nmr (CDCl$_3$). $\delta$2.07 (s, 3H), 3.77 and 4.27 (ABq, 2H, J=16 Hz), 3.87 (s, 3H), 5.05 (s, 1H), 5.50 (d, J=2 Hz, 1H), 6.08 (d, J=2 Hz, 1H), 7.87 (br.s, 4H).

In the same manner as described in Examples 13–15, but using as starting materials the methyl, ethyl, propyl, isopropyl, t-butyl, trichloroethyl, benzyl, p-nitrobenzyl, or benzhydryl esters of 7-phenylacetamido-3-chloro-, -3-bromo-, or -3-iodo - 3 methylcepham-4-carboxylic acid and using chlorine, sulfuryl chloride, bromine, or sulfuryl bromide as the halogenating agent, the methyl, ethyl, propyl, isopropyl, t-butyl, trichloroethyl, benzyl, p-nitrobenzyl, and benzhydryl esters of 3-S-phenylacetamido-, 3S-p-chlorophenylacetamido-, 3S-p-bromophenylacetamido-4S(trans)-chloro- or -bromo-azetidinone-1-$\alpha$($\beta$-methylsulfenylchloride—or $\beta$-methylsulfenylbromide-$\beta$-chloro-, $\beta$-bromo-, or $\beta$-iodo)butyric acid are obtained, respectively.

We claim:
1. A compound of formula 1

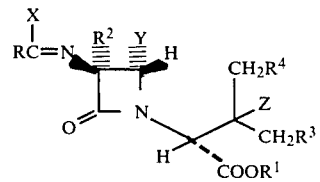

wherein R is an amino-protecting group commonly used in penicillin chemistry derivatives selected from the group consisting of H, $C_1$–$C_6$ alkyl, phenyl (optionally substituted in the o—, m—, or p- positions by $CH_3$, F, Cl, $OCH_3$, or a nitro group), benzyl, 2-thienylmethyl, tetrazol (1-, 2-, or 5-)ylmethyl, 2-phenyl-5-methylisoxazol-4-yl, phenoxymethyl, and $R^5O$— and $R^5S$, wherein $R^5$ stands for $C_1$–$C_6$ alkyl, phenyl, benzyl or trichloroethyl; X is OH, and RCX=N may also represent the phthalimido, succinimido-, or tritylamino- group; $R^1$ is a carboxy-protecting group commonly used in penicillin chemistry selected from the group consisting of hydrogen, a cleavable acid protective group selected from $C_1$–$C_6$ alkyl, methoxymethyl, phenoxymethyl, benzyloxymethyl, trichloroethyl, benzyl, p-halobenzyl, p-nitrobenzyl, p-methoxybenzyl, benzhydryl and trimethylsilyl; $R^2$ is selected from hydrogen and methoxy; $R^3$ and $R^4$ are selected from the group consisting of H, Cl, Br, I, OCHO, $OCOCH_3$, SCl, and SBr with the proviso that one and only one of $R^3$ or $R^4$ must be H, Y is selected from Cl and Br, Z is selected from Cl, Br, I, SCl, and SBr and one of $R^3$, $R^4$ and Z must be SCl or SBr.

2. 2,2,2-Trichloroethyl 3-S-phenoxyacetamido-4S(trans)-chloroazetidinone-1-α(β-chloromethyl-β-sulfenylchloride)butyrate, as claimed in claim 1.

3. 2,2,2-Trichloroethyl 3-S-phenoxyacetamido-4S(trans)-chloroazetidinone-1-α(β-bromomethyl-β-sulfenylchloride)butyrate, as claimed in claim 1.

4. 2.2.2-Trichloroethyl 3-S-phenoxyacetamido-4S(trans)-chloroazetidinone-1-α(β-iodomethyl-β-sulfenylchloride)butyrate, as claimed in claim 1.

5. Methyl 3-S-phenoxyacetamido-4S(trans)-chloroazetidinone-1-α(β-acetoxymethyl-β-sulfenylchloride)butyrate, as claimed in claim 1.

6. 2,2,2-Trichloroethyl 3S-p-chlorophenoxyacetamido-4S(trans)chloroazetidinone-1-α(β-chloromethyl-β-sulfenylchloride)butyrate, as claimed in claim 1.

7. Methyl 3S-p-chlorophenoxyacetamido-4S(trans)-chloroazetidinone-1-α(β-chlorosulfenylmethyl-β-chloro)butyrate, as claimed in claim 1.

8. Benzhydryl 3S-phenoxyacetamido-4S(trans)-chloroazetidinone-1-α(β-chlorosulfenylmethyl-β-bromo)butyrate, as claimed in claim 1.

9. Methyl 3S-phthalimido-4S(trans)-chloroazetidinone-1-α(β-methylsulfenylchloride-β-chloro)butyrate, as claimed in claim 1.

10. A compound according to claim 1 wherein Z is SCl or SBr.

11. A compound according to claim 1 wherein Z is Cl, Br or I, one of $R^3$ and $R^4$ is hydrogen and the other is OCHO or $OCOCH_3$.

* * * * *

UNITED STATES PATENT AND TRADEMARK OFFICE
CERTIFICATE OF CORRECTION

PATENT NO. : 4,187,221
DATED      : February 5, 1980
INVENTOR(S): Donald Micetich, Robert Fortier, Chia C. Shaw and Werner Merlo It is certified that error appears in the above—identified patent and that said Letters Patent is hereby corrected as shown below:

In the cover sheet, item 30

Foreign Application Priority Data

"December 31, 1976, United Kingdom 54407/76

Signed and Sealed this

Tenth Day of June 1980

[SEAL]

Attest:

SIDNEY A. DIAMOND

Attesting Officer

Commissioner of Patents and Trademarks